United States Patent

Grohe

Patent Number: 5,182,401
Date of Patent: Jan. 26, 1993

[54] PREPARATION OF 3-AMINO-2-(HET)AROYL-ACRYLIC ACID DERIVATIVES

[75] Inventor: Klaus Grohe, Odenthal, Fed. Rep. of Germany

[73] Assignee: Bayer Aktiengesellschaft, Leverkusen, Fed. Rep. of Germany

[21] Appl. No.: 694,692

[22] Filed: May 2, 1991

[30] Foreign Application Priority Data

May 12, 1990 [DE] Fed. Rep. of Germany ....... 4015299

[51] Int. Cl.$^5$ .......................................... C07D 213/50
[52] U.S. Cl. .................................. 546/287; 546/156; 546/288; 546/289; 546/296; 546/297; 546/298; 546/307; 546/310; 546/315; 558/405; 560/17; 560/22; 560/23; 560/51; 560/53; 564/251; 564/313; 564/341; 564/343
[58] Field of Search ............... 564/151, 313, 314, 341, 564/343, 251; 558/405; 560/17, 22, 23, 51, 53; 546/156, 287, 288, 289, 296, 297, 298, 307, 310, 315; 544/363

[56] References Cited

U.S. PATENT DOCUMENTS

| | | | |
|---|---|---|---|
| 3,317,538 | 5/1967 | Freed et al. | 564/343 |
| 3,488,737 | 1/1970 | Gordon | 564/343 |
| 3,591,593 | 7/1971 | Thiele et al. | 564/343 |
| 4,317,930 | 3/1982 | Hirose et al. | 564/343 |
| 5,073,556 | 12/1991 | Iwata et al. | 546/146 |
| 5,075,319 | 12/1991 | Lesher et al. | 546/146 |

FOREIGN PATENT DOCUMENTS

646704  8/1962 Canada .................. 564/343

*Primary Examiner*—C. Warren Ivy
*Assistant Examiner*—James H. Turnipseed
*Attorney, Agent, or Firm*—Sprung Horn Kramer & Woods

[57] ABSTRACT

A process for the preparation of a 3-amino-2-(het)aroyl-acrylic acid derivative fo the formula

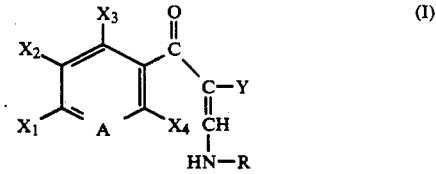

in which
Y represents a nitrile, or an ester group, —COOR$_1$, or an acetyl group, where
R$^1$ denotes C$_1$–C$_4$-alkyl, and
R denotes optionally substituted alkyl, cyclopropyl, alkoxy, phenyl or amino,
A represents nitrogen or C—R$_2$, where
R$_2$ denotes hydrogen, methyl, halogen, nitro, methoxy or cyano,
X$_1$ and X$_2$ are identical or different and denote halogen, and
X$_3$ denotes hydrogen, halogen or nitro and
X$_4$ denotes halogen, nitro, methoxy or methylthio, which comprises reacting a 3-dialkylamino-2-(het)aroyl-acrylic acid derivative of the formula

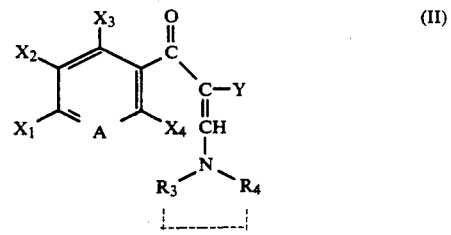

in which
R$_3$ and R$_4$ are the same or different and represent an alkyl group having 1 to 4 carbon atoms, or, together with the nitrogen atom to which they are bonded, form a ring,
with a primary amine of the formula R—NH$_2$ in the presence of at least one equivalent of an acid HX in a solvent or in excess acid.

7 Claims, No Drawings

PREPARATION OF 3-AMINO-2-(HET)AROYL-ACRYLIC ACID DERIVATIVES

The present invention relates to a process for the preparation of 3-amino-2-(het)aroyl-acrylic acid derivatives, which are useful intermediates for the synthesis of highly active antibacterial medicaments.

It is known that 3-amino-2-benzoylacrylic acid derivatives which are monosubstituted on the nitrogen atom are obtained when 3-dialkylamino-2-benzoylacrylic acid derivatives are reacted with primary aliphatic amines in inert organic solvents such as, for example, cyclohexane, toluene, chlorobenzene or butyleneglycol at relatively high temperature (EP 176,846, EP 300,311). A disadvantage of this process is that, under the reaction conditions, the dialkylamine released during the reaction attacks reactive halogen atoms on the ring in a side reaction. Compound mixtures which can only be separated with difficulty and are therefore unsuitable for the subsequent reactions may then be obtained.

It has now been found that 3-amino-2-(het)aroyl-acrylic acid derivatives of the formula (I)

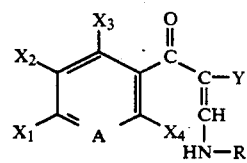

in which

Y represents a nitrile or ester group -COOR$_1$ and also an acetyl group, where
R$_1$ denotes C$_1$-C$_4$-alkyl and
R can be alkyl having 1 to 6 carbon atoms, 2-fluoroethyl, 2-chloroethyl, 2-hydroxyethyl, 1-(hydroxymethyl)-ethyl, cyclopropyl, methoxy, 4-fluorophenyl, 2,4-difluorophenyl, dimethylamino, formylmethylamino or isopropylideneamino,
A represents nitrogen or C-R$_2$, where
R$_2$ can be hydrogen, methyl, halogen, nitro, methoxy or cyano,
X$_1$ can be halogen, preferably chlorine or fluorine, and
X$_2$ represents halogen, preferably fluorine, and
X$_3$ denotes hydrogen, halogen or nitro and
X$_4$ can be halogen, preferably chlorine or fluorine, nitro, methoxy or methylthio,
are obtained when 3-dialkylamino-2-(het)aroyl-acrylic acid derivatives of the formula (II)

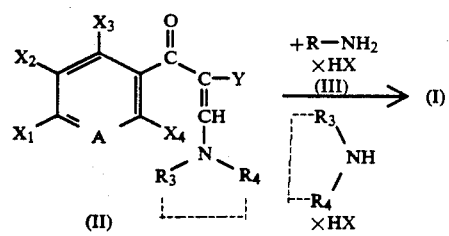

in which

A, X$_1$-X$_4$ and Y have the abovementioned meanings and R$_3$ and R$_4$ can be the same or different and represent an alkyl group having 1 to 4 carbon atoms or, together with the nitrogen atom to which they are bonded, form a 5- or 6-membered ring which additionally can contain the atoms or groups —O—, —S— or —SO$_2$—, are reacted with primary amines (III), in which R has the abovementioned meaning, in the presence of at least one equivalent of an acid in a solvent or in excess acid.

It must be considered as decidedly surprising that the 3-dialkylamino-2-(het)aroyl-acrylic acid derivatives (II) react with the salts (III) to give (I).

A particular advantage of this new process is that reactive halogen atoms present in the (het)aryl ring of (II) do not react with the amine salts. Pure intermediates (I) suitable for the subsequent reactions are therefore obtained directly.

If ethyl 3-dimethylamino-2-(2,3,4,5-tetrafluorobenzoyl)acrylate (1), cyclopropylamine (2) and acetic acid are used as starting substances, the course of the reaction according to the invention can be reproduced by the following equation:

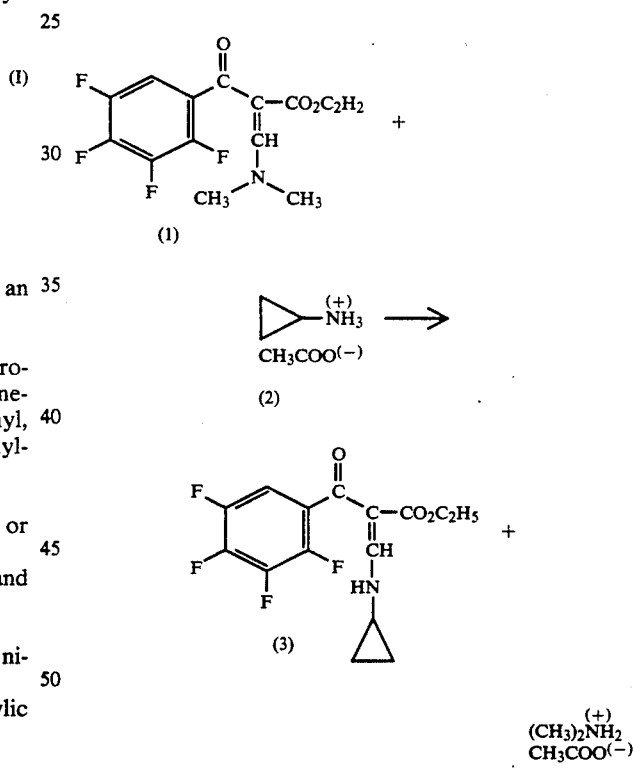

The dimethylamine formed in the reaction of (1) with (2) to give (3) is captured as the acetate salt (4). Reaction with the activated 2- or 4-fluorine atom of (1) or (3) is thus avoided.

The quinolonecarboxylic ester (5) is formed in the subsequent cyclization of (3) and is hydrolyzed to the acid (6) and, after replacement of the 7-fluorine atom by secondary amine radicals, yields the 7-aminoquinolonecarboxylic acids (7) of high antibacterial activity.

(3) → 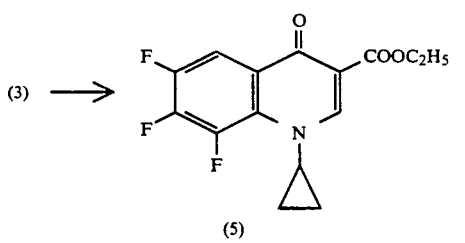 →

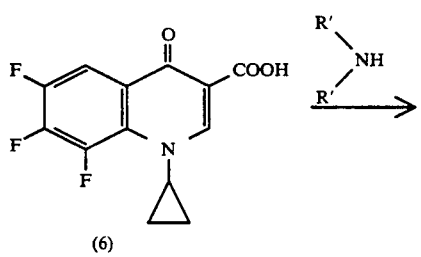

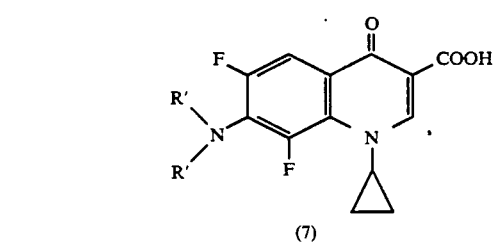

The amines III which can be used according to the invention are known. Examples are: methylamine, ethylamine, 2-fluoroethylamine, 2-hydroxyethylamine, isopropylamine, tert.-butylamine, cyclopropylamine, O-methylhydroxylamine, 4-fluoroaniline, 2,4-difluoroaniline, 1-formyl-1-methylhydrazine and 1,1-dimethylhydrazine.

The acrylic acid derivatives II are also known or can easily be prepared by known methods (EP 176,846, EP300,311). Examples are: ethyl 3-dimethylamino-2-(2,4,5-trifluorobenzoyl)-acrylate, ethyl 3-dimethylamino-2-(2,4-dichloro-5-fluorobenzoyl)-acrylate, 3-dimethylamino-2-(2,4-dichloro-5-fluorobenzoyl)-acrylonitrile, methyl 3-pyrrolidino-2-(2,4-dichloro-5-fluorobenzoyl)-acrylate, ethyl 3-dimethylamino-2-(2,3,4,5-tetrafluorobenzoyl)-acrylate, 3-dimethylamino-2-(2,3,4,5-tetrafluorobenzoyl)-acrylonitrile, ethyl 3-dimethylamino-2-(2,4-dichloro-5-fluoro-3-nitrobenzoyl)-acrylate, ethyl 3-dimethylamino-2-(2,3,4,5,6-pentafluorobenzoyl)-acrylate, ethyl 3-dimethylamino-2-(3-chloro-2,4,5-trifluorobenzoyl)-acrylate, ethyl 3-dimethylamino-2-(2,4-dichloro-3,6-difluorobenzoyl)-acrylate, ethyl 3-diethylamino-2-(2,3,4,5-tetrafluorobenzoyl)-acrylate, methyl 3-morpholino-2-(2,4-dichloro-5-fluorobenzoyl)-acrylate, ethyl 3-dimethylamino-2-(2,6-dichloro-5-fluoronicotinyl)-acrylate, 3-dimethylamino-2-(2,6-dichloro-5-fluoronicotinyl)-acrylonitrile and ethyl 3-dimethylamino-2-(2,6-dichloronicotinyl)-acrylate.

In the process according to the invention, II is reacted with a salt of an organic or inorganic acid of III in an organic solvent or diluent. Examples of diluents which can be used are acetic acid, propionic acid, glycolic acid, toluene, chloroform, dioxane, dimethyl sulphoxide, N-methylpyrrolidone, dimethylformamide or tetramethylurea.

Suitable organic or inorganic acids are, for example, acetic acid, propionic acid, glycolic acid, hydrochloric acid, methanesulphonic acid, p-toluenesulphonic acid, lactic acid, citric acid, tartaric acid, malic acid, succinic acid, maleic acid or fumaric acid, which can be employed alone or mixed.

The reaction is carried out at temperatures between 10° C. and 150° C., preferably between 20° C. and 100° C. It is preferably carried out at normal pressure.

The reaction components II and III are employed in a molar ratio of 1:1 to 1:4, preferably 1:1 to 1:1.1.

Several process variants can be used in the reaction of II with III to give I:

a) The dialkylaminoacrylic acid ester or the corresponding nitrile II is initially introduced in acetic acid and the amine III is added dropwise or in portions.

b) A salt of the amine III is added in portions or a solution of this salt in acetic acid is added dropwise to a solution or suspension of II in acetic acid.

c) The amine III is added dropwise to the acetic acid and then a solution of II in acetic acid is added dropwise or II is introduced in portions. A salt of the amine III with another acid can also be initially introduced in acetic acid.

d) The corresponding salt of the amine III is added in portions to a solution or suspension of II in an inert diluent such as, for example, toluene.

e) The amine salt is initially introduced in an inert diluent such as, for example, toluene and II is added in portions or dropwise dissolved in toluene.

The mixture is stirred at 10° C. to 150° C., preferably at 20° C. to 100° C., for 0.5 hour to 48 hours, preferably for 2 to 12 hours.

For working up, the diluent is distilled off in vacuo, the residue is taken up in methylene chloride/water, the organic phase is washed with water and dried using sodium sulphate and the methylene chloride is distilled off.

If a water-miscible diluent such as, for example, acetic acid, dioxane or ethanol is used, the reaction mixture can also be poured onto ice, and the precipitate filtered off with suction and dried.

The crude products of I are either directly further reacted or first purified by recrystallization.

EXAMPLE 1

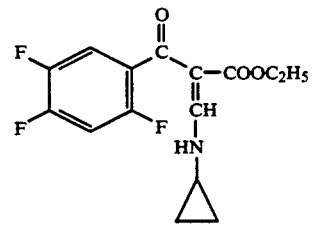

a) The solution from 6.3 g of cyclopropylamine in 40 ml of glacial acetic acid is added dropwise with stirring at 10° C. to 15° C. to a solution of 29 g of ethyl 3-dimethylamino-2-(2,4,5-trifluorobenzoyl)-acrylate in 100 ml of glacialacetic acid. The mixture is stirred at room temperature for 6 hours and then warmed to 50° C. to 60° C. for 2 hours. The solvent is then distilled off in vacuo, the residue is taken up in methylene chloride/water, washed with water and saturated NaHCO$_3$ solution and dried over sodium sulphate, and the methylene chloride is distilled off.

Crude yield: 27.5 g (91.2%) of ethyl 3-cyclopropylamino-2-(2,4,5-trifluorobenzoyl)-acrylate of melting point 54° C. to 56° C.

b) First 34.7 g of cyclopropylamine and then a solution of 182.7 g of ethyl 3-dimethylamino-2-(2,4,5-trifluorobenzoyl)-acrylate in 100 ml of glacial acetic acid are added dropwise with stirring at about 10° C. to 200 ml of glacial acetic acid. The mixture is stirred at room temperature for 12 hours and at 50° C. to 60° C. for 2 hours. Working-up is carried out as described under (a).

Yield: 171 g (90%) of ethyl 3-cyclopropylamino(2,4,5-trifluorobenzoyl)-acrylate of melting point 54° C. to 56° C.

EXAMPLE 2

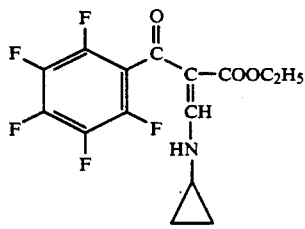

First 1.3 g of cyclopropylamine and then a solution of 6.74 g of ethyl 3-dimethylamino-2-(2,3,4,5,6-pentafluorobenzoyl)-acrylate in 25 ml of glacial acetic acid are added dropwise to 10 ml of glacial acetic acid while cooling with cold water. The mixture is stirred at room temperature for 2 hours and at 50° C. to 60° C. for 2 hours. Working-up is carried out as under (1a).

Yield: 6.8 g (97.4%) of ethyl 3-cyclopropylamino-2-(2,3,4,5,6-pentafluorobenzoyl)-acrylate; melting point of a sample after recrystallisation from cyclohexane/light petroleum: 84° C. to 85° C.

EXAMPLE 3

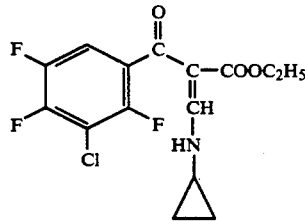

1.41 g of cyclopropylamine and then a solution of 7.3 g of ethyl 3-dimethylamino-2-(3-chloro-2,4,5-trifluorobenzoyl)-acrylate in 25 ml of glacial acetic acid are added dropwise to 11 ml of glacial acetic acid while cooling with cold water and stirring. The mixture is stirred at room temperature for 12 hours and then at 50°-60° C. for 2 hours. Working-up is carried out as indicated under (1a).

Yield: 7.3 g of ethyl 3-cyclopropylamino-2-(3-chloro-2,4,5-trifluorobenzoyl)-acrylate of melting point 78°-79° C. (after recrystallization from ethanol/water).

EXAMPLE 4

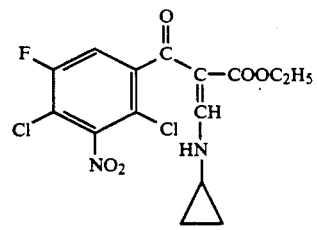

a) 6.6 g of cyclopropylamine are added dropwise to 150 ml of glacial acetic acid while stirring and cooling with cold water. 37.9 g of ethyl 3-dimethylamino-2-(2,4-dichloro-5-fluoro-3-nitrobenzoyl)-acrylate are then added in portions. The mixture is stirred at room temperature for 12 hours and then at 50° C. to 60° C. for 1 hour. The hot solution is poured onto ice, and the precipitate is filtered off with suction, washed with water and dried.

Yield: 36.5 g (93.3%) of ethyl 3-cyclopropylamino-2-(2,4-dichloro-5-fluoro-3-nitrobenzoyl)-acrylate. Sample after recrystallization from ethanol/water of melting point 146° C. to 147° C.

b) First 1.5 g of glacial acetic acid and then a solution of 7 4 g of ethyl 3-dimethylamino-2-(2,4-dichloro-5-fluoro-3-nitrobenzoyl)-acrylate in 30 ml of toluene are added dropwise with ice-cooling and stirring to a solution of 1.25 g of cyclopropylamine in 30 ml of toluene. The mixture is stirred at room temperature for 1 hour and at 70° C. to 80° C. for 2 hours. The cooled solution is washed with water and sodium bicarbonate solution and dried with sodium sulphate, and the solvent is distilled off in vacuo.

Yield: 7.5 g (98%) of ethyl 3-cyclopropylamino-2-(2,4-dichloro-5-fluoro-3-nitrobenzoyl)-acrylate of melting point 139° C. to 141° C.

EXAMPLE 5

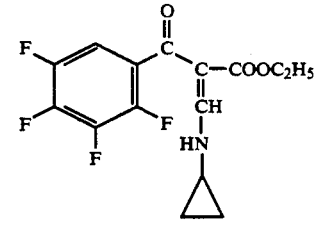

6 g of cyclopropylamine and then a solution of 29.2 g of ethyl 3-dimethylamino-2-(2,3,4,5-tetrafluorobenzoyl)-acrylate are added dropwise while stirring and cooling with cold water to 50 ml of glacial acetic acid. The mixture is stirred at room temperature for 6 hours and at 50° C. to 60° C. for 2 hours and the solvent is then distilled off in vacuo. Working-up is carried out as described under (1a).

Yield: 29.7 g (98%) of ethyl 3-cyclopropylamino-2-(2,3,4,5-tetrafluorobenzoyl)-acrylate of melting point 64° C. After recrystallisation from cyclohexane/light petroleum the melting point is 66° C. to 68° C.

EXAMPLE 6

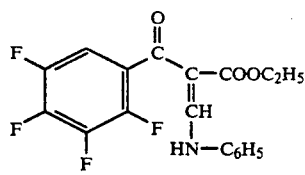

3 3 g of aniline and a solution of 10 9 of ethyl 3-dimethylamino-2-(2,3,4,5-tetrafluorobenzoyl)-acrylate in 60 ml of glacial acetic acid are added dropwise while stirring and cooling with cold water to 10 ml of glacial acetic acid. The mixture is stirred at room temperature for 2 hours and at 70° C. to 80° C. for 2 hours and is worked up as described under (1a).

Crude yield: 10 g (86.9%) of ethyl 3-anilino-2-(2,3,4,5-tetrafluorobenzoyl)-acrylate. A sample is recrystallised from cyclohexane. Melting point: 91° C.

EXAMPLE 7

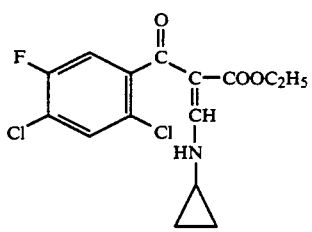

a) 1.35 g of cyclopropylamine are added dropwise at about 10° C with stirring to a solution of 6.6 g of ethyl 3-dimethylamino-2-(2,4-dichloro-5-fluorobenzoyl)-acrylate in 40 ml of glacial acetic acid. The mixture is stirred at room temperature for 12 hours or at room temperature for 30 minutes and at 80° C. for 1.5 hours and is worked up according to Example (1a).

Yield: 6.7 g (97.9 %) of ethyl 3-cyclopropylamino-2-(2,4-dichloro-5-fluorobenzoyl)-acrylate of melting point 87° C. to 88° C.

b) 1.35 g of cyclopropylamine are added dropwise to a solution of 1.5 g of glacial acetic acid in 60 ml of chloroform. 6.6 g of ethyl 3-dimethylamino-2-(2,4-dichloro-5-fluorobenzoyl)-acrylate are then added in portions, and the mixture is stirred at room temperature for 1 hour and heated under reflux for 3 hours. The reaction mixture is then washed with water and sodium bicarbonate solution, and the organic phase is dried with sodium sulphate and the solvent is distilled off.

Yield: 6.5 9 (95 %) of ethyl 3-cyclopropylamino-2-(2,4-dichloro-5-fluorobenzoyl)-acrylate of melting point 84° C. to 86° C.

c) 1.1 g of methanesulphonic acid are added dropwise with ice-cooling and stirring to a solution of 0.63 g of cyclopropylamine in 30 ml of toluene. 2.8 g of ethyl 3-dimethylamino-2-(2,4-dichloro-5-fluorobenzoyl)-acrylate are then added in portions, and the mixture is stirred at room temperature for 1 hour and at 70° C. to 80° C. for 2 hours. The suspension is washed with water and sodium bicarbonate solution and dried with sodium sulphate, and the solvent is distilled off in vacuo.

Yield: 2.9 g (96.5%) of ethyl 3-cyclopropylamino-2-(2,4-dichloro-5-fluorobenzoyl)-acrylate of melting point 88° C. to 89° C.

EXAMPLE 8

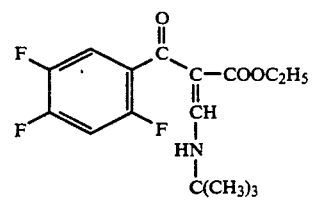

At about 10° .C, 8 g of tert.-butylamine are added dropwise with stirring to 50 ml of glacial acetic acid. A solution of 32 g of ethyl 3-dimethylamino-2-(2,4,5-trifluorobenzoyl)acrylate in 80 ml of glacial acetic acid is then added dropwise, and the mixture is stirred at room temperature for 12 hours and worked up as described in Example (1a).

Crude yield: 28.5 g (81.5%) of ethyl 3-tert.-butylamino-2-(2,4,5-trifluorobenzoyl)-acrylate. A sample is recrystallized from cyclohexane/light petroleum. Melting point 100° C. to 101° C.

EXAMPLE 9

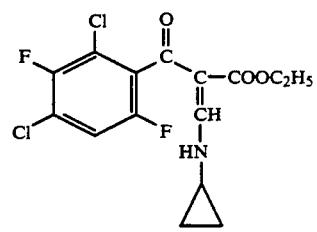

18.8 g of cyclopropylamine and then a solution of 105 g of ethyl 3-dimethylamino-2-(2,4-dichloro-3,6-difluorobenzoyl)-acrylate in 130 ml of glacial acetic acid are added dropwise while stirring and cooling with cold water to 140 ml of glacial acetic acid. The mixture is stirred at room temperature for 12 hours and at 50° C. to 60° C. for 2 hours and is worked up as in Example (1a).

Yield: 83 g (76.4%) of ethyl 3-cyclopropylamino-2-(2,4-dichloro-3,6difluorobenzoyl)-acrylate of melting point 98° to 100° C.

EXAMPLE 10

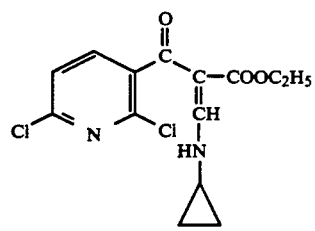

0.6 g of cyclopropylamine in glacial acetic acid is reacted with 3.17 g of ethyl 3-dimethylamino-2-(2,6-dichloronicotinyl)-acrylate analogously to Example (4a) and ethyl 3-cyclopropylamine-2-(2,6-dichloronicotinyl)-acrylate of melting point 131° C. to 133° C. is obtained in a yield of 94% of theory.

EXAMPLE 11

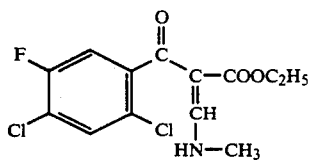

0.74 g of methylamine hydrochloride is added to a solution of 3.3 g of ethyl 3-dimethylamino-2-(2,4-dichloro-5-fluorobenzoyl)-acrylate in 30 ml of toluene, and the mixture is stirred at room temperature for 1 hour and at 70° C. to 80° C. for 4 hours. Working-up is carried out as in Example (7c).

Yield: 3.0 g (94.9 %) of ethyl 3-methylamino-2-(2,4-dichloro-5-fluorobenzoyl)-acrylate of melting point 95° C. to 97° C.

Examples 12 to 37 can also be prepared in comparable yields analogously to Examples 1 to 11 by the process according to the invention.

| Ex. No. | $X_1$ | $X_2$ | $X_3$ | $X_4$ | A | Y | R | Melting point [°C.] |
|---|---|---|---|---|---|---|---|---|
| 12 | Cl | F | H | Cl | CH | $COOC_2H_5$ | $C(CH_3)_3$ | 91–92 |
| 13 | Cl | F | H | Cl | CH | $COOCH_3$ | cyclopropyl | 146–148 |
| 14 | Cl | F | H | Cl | CH | CN | cyclopropyl | 93–95 |
| 15 | Cl | F | H | $CH_3O$ | CH | $COOCH_3$ | cyclopropyl | 130–132 |
| 16 | Cl | F | H | Cl | CH | CN | 4-F-phenyl | 195–197 |
| 17 | F | F | H | F | CF | $COOC_2H_5$ | 4-F-phenyl | 93–95 |
| 18 | F | F | H | F | CF | $COOC_2H_5$ | 3,4-di-F-phenyl | 114–116 |
| 19 | Cl | F | H | Cl | $C-NO_2$ | $COO_2H_5$ | 4-F-phenyl | 129–131 |
| 20 | Cl | F | H | Cl | $C-NO_2$ | $COOCH_3$ | cyclopropyl | 168–169 |
| 21 | Cl | F | H | Cl | $C-NO_2$ | $COOC_2H_5$ | $FCH_2CH_2$ | 123–124 |
| 22 | Cl | F | H | Cl | CH | $COOC_2H_5$ | 3,4-di-F-phenyl | 102–104 |
| 23 | F | F | H | F | CF | $COOC_2H_5$ | $CH_3$ | 155–157 |

-continued

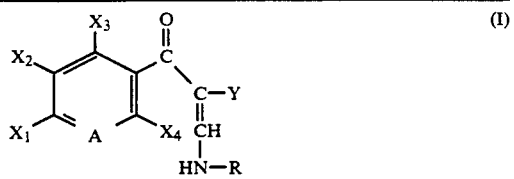

| Ex. No. | X₁ | X₂ | X₃ | X₄ | A | Y | R | Melting point [°C.] |
|---|---|---|---|---|---|---|---|---|
| 24 | F | F | H | F | CH | COOCH$_3$ | cyclopropyl | 123–125 |
| 25 | Cl | F | H | Cl | CH | COOC$_2$H$_2$ | (CH$_3$)$_2$CH— | 97–98 |
| 26 | F | F | H | F | CH | COOC$_2$H$_5$ | 2,4-difluorophenyl | 107–109 |
| 27 | Cl | F | Cl | F | CH | COOC$_2$H$_5$ | cyclopropyl | 106–108 |
| 28 | Cl | F | Cl | F | CH | COOC$_2$H$_5$ | 2,4-difluorophenyl | 91–93 |
| 29 | F | F | H | F | C—Cl | COOC$_2$H$_5$ | 2,4-difluorophenyl | 128–130 |
| 30 | F | F | F | F | C—F | COOC$_2$H$_5$ | 2,4-difluorophenyl | 99–101 |
| 31 | Cl | F | H | Cl | C—H | COOC$_2$H$_5$ | HOCH$_2$CH$_2$— | 90–92 |
| 32 | F | F | H | F | C—F | COOC$_2$H$_5$ | CH$_3$CH$_2$— | 115–117 |
| 33 | F | F | H | F | C—F | COOC$_2$H$_5$ | CH$_3$O— | 152–153 |
| 34 | Cl | F | H | Cl | C—NO$_2$ | COOC$_2$H$_5$ | CH$_3$CH$_2$— | 143–145 |
| 35 | Cl |  | H | Cl | N | COOC$_2$H$_5$ | cyclopropyl | 131–133 |
| 36 | Cl | F | H | Cl | N | COOC$_2$H$_5$ | 4-fluorophenyl | 112–114 |
| 37 | Cl | F | H | Cl | N | COOC$_2$H$_5$ | 2,4-difluorophenyl | 138–140 |

EXAMPLE 38

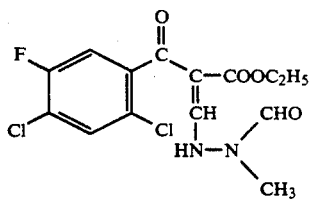

0.82 g of 1-formyl-1-methylhydrazine is added dropwise to 30 ml of glacial acetic acid while stirring and cooling with cold water. 3.3 g of ethyl 3-dimethylamino-2-(2,4-dichloro-5-fluorobenzoyl)-acrylate are then added in portions, the mixture is stirred at room temperature for 1.5 hours and at 50° C. to 60° C. for 2 hours and the solvent is distilled off in vacuo. Working-up is carried out as described under Example (1a).

Yield: 2.9 g (80.9 %) of ethyl 3-(2-formyl-2-methylhydrazino)-2-(2,4-dichloro-5-fluorobenzoyl)-acrylate of melting point 104° C. to 106° C. (after recrystallization from cyclohexane/light petroleum).

Glacial acetic acid process

EXAMPLE 39 (cf. Example 5)

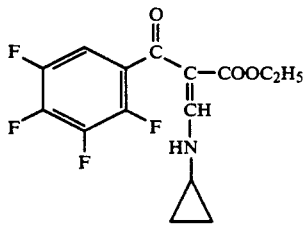

1.2 g of cyclopropylamine are added dropwise to 50 ml of glacial acetic acid while stirring and cooling with cold water. 6.38 g of ethyl 3-dimethylamino-2-(2,3,4,5-tetrafluorobenzoyl)-acrylate are then added in portions and rinsed in with about 10 ml of ethanol. The mixture is stirred at room temperature for 6 hours and then allowed to stand at room temperature overnight, and the solvents are distilled off in vacuo. Working-up is carried out as described under (1a).

Yield: 6 g of melting point 57 to 59° C.

Cyclization to the quinolonecarboxylic acid ester:

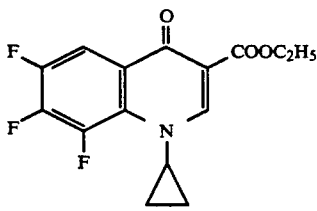

3.31 g (0.01 mol) of ethyl 3-cyclopropylamino-2-(2,3,4,5-tetrafluorobenzoyl)-acrylate, 0.65 g of sodium fluoride and 20 ml of N-methylpyrrolidone are heated to 140° C. for 3 hours. The mixture is poured into 100 ml of water and the precipitate is filtered off with suction and then washed well with water. After drying in vacuo at 100° C., 2.8 g (90%) of ethyl 1-cyclopropyl-6,7,8-trifluoro-1,4-dihydro-4-oxo-quinolinecarboxylate of melting point 156° to 159° C. are obtained. According to the $^1$H-NMR spectrum recorded in chloroform, the product contains no ethyl 7-dimethylamino-1-cyclopropyl-6,8-difluoro-1,4-dihydro-4-oxo-quinolinecarboxylate.

B) Toluene process

EXAMPLE 40

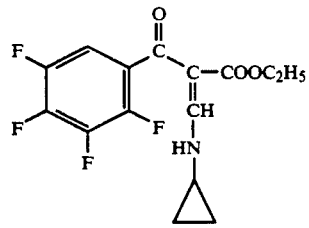

6.38 g (0.02 mol) of ethyl 3-dimethylamino-2-(2,3,4,5-tetrafluorobenzoyl)-acrylate are heated to boiling under reflux with 1.2 g of cyclopropylamine and 30 ml of toluene until the evolution of gas is complete (about 1 hour). The solvent is then distilled off in vacuo and the residue is worked up as in (1a).

Yield: 5.9 g of melting point 56° to 58° C.

Cyclization to the quinolonecarboxylic acid ester: 3.31 g (0.01 mol) of ethyl 3-cyclopropylamino-2-(2,3,4,5-tetrafluorobenzoyl)-acrylate obtained by the toluene process, 0.65 g of sodium fluoride and 20 ml of N-methylpyrrolidone are heated to 140° C. for 3 hours. The mixture is poured into 100 ml of water and the precipitate is filtered off with suction and then washed well with water. After drying in vacuo at 100° C., 2.8 g (90%) of ethyl 1-cyclopropyl-6,7,8-trifluoro-1,4-dihydro-4-oxo-quinolinecarboxylate of melting point 149° to 152° C. are obtained. According to the $^1$H-NMR spectrum recorded in chloroform, the product contains about 7 mol-% of ethyl 1-cyclopropyl-7-dimethylamino-6,8-difluoro-1,4-dihydro-4-oxo-quinolinecarboxylate.

It will be appreciated that the instant specification is set forth by way of illustration and not limitation and that various modifications and changes may be made without departing from the spirit and scope of the present invention.

What is claimed is:

1. A process for the preparation of a 3-amino-2-(het-)aroylacrylic acid derivative of the formula

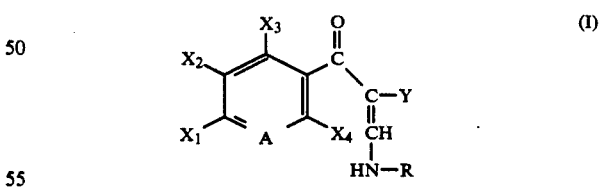

in which

Y represents a nitrile, an ester group —COOR$_1$, or an acetyl group,

R$^1$ denotes C$_1$–C$_4$-alkyl and

R denotes alkyl having 1 to 6 carbon atoms, 2-fluoroethyl, 2-chloroethyl, 2-hydroxyethyl, 1-(hydroxymethyl)-ethyl, cyclopropyl, methoxy, 4-fluorophenyl, 2,4-difluorophenyl, dimethylamino, formylmethylamino or isopropylideneamino, A represents nitrogen or C-R$_2$, where R$_2$ denotes hydrogen, methyl, halogen, nitro, methoxy or cyano, $X_1$ and $X_2$ are identical or different and denote halogen, and $X_3$ denotes hydrogen, halogen or nitro and $X_4$ denotes halogen, nitro, methoxy or methylthio, which comprises reacting a 3-dialkylamino-2-(het-)aroylacrylic acid derivative of the formula

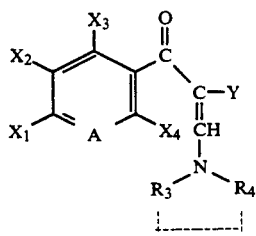

(II)

in which $R_3$ and $R_4$ are the same or different and represent an alkyl group having 1 to 4 carbon atoms or, together with the nitrogen atom to which they are bonded, form a 5- or 6-membered ring which additionally can contain the atoms or groups $-O-$, $-S-$ or $-SO_2-$, with a primary amine of the formula $R-NH_2$ in the presence of at least one equivalent of an acid HX in a solvent or in excess acid.

2. A process according to claim 1, in which $X_1$ denotes chlorine or fluorine, $X_2$ denotes fluorine, and $X_3$ denotes hydrogen, chlorine, fluorine or nitro, $X_4$ denotes chlorine, fluorine, nitro, methoxy or methylthio.

3. A process according to claim 1, wherein the reaction is carried out at a temperature from about 10° C. to 150° C.

4. A process according to claim 1, wherein the molar ratio of the acid HX to the amine $R-NH_2$ is about 1:1 to 4:1.

5. A process according to claim 1, wherein the acid HX is at least one member selected from the group consisting of acetic acid, propionic acid, glycolic acid, hydrochloric acid, methanesulphonic acid, p-toluenesulphonic acid, lactic acid, citric acid, tartaric acid, malic acid, succinic acid, maleic acid and fumaric acid.

6. A process according to claim 1, wherein the reaction is carried out in a member selected from the group consisting of acetic acid, toluene, chloroform and dioxane.

7. A process according to claim 2, wherein the reaction is carried out at a temperature from about 10° C. to 150° C., the acid HX is at least one member selected from the group consisting of acetic acid, propionic acid, glycolic acid, hydrochloric acid, methanesulphonic acid, p-toluenesulphonic acid, lactic acid, citric acid, tartaric acid, malic acid, succinic acid, maleic acid and fumaric acid and the reaction is carried out in a member selected from the group consisting of acetic acid, toluene, chloroform and dioxane.

* * * * *